US006406293B1

(12) United States Patent
Burstein

(10) Patent No.: US 6,406,293 B1
(45) Date of Patent: Jun. 18, 2002

(54) HAND-HELD DENTAL TRANSILLUMINATING DEVICE

(75) Inventor: James A. Burstein, Toronto (CA)

(73) Assignee: Burstein Enterprises Incorporated, Toronto (CA)

( * ) Notice: Subject to any disclaimer, the term of this patent is extended or adjusted under 35 U.S.C. 154(b) by 0 days.

(21) Appl. No.: 09/684,651

(22) Filed: Oct. 10, 2000

(51) Int. Cl.[7] .................................................. A61C 1/00
(52) U.S. Cl. ......................................... 433/29; 600/245
(58) Field of Search ........................... 433/29; 600/245, 600/241, 175, 182; 362/804, 572, 573, 581, 582

(56) References Cited

U.S. PATENT DOCUMENTS 2,186,143 A * 1/1940 Neugass ..................... 600/245
3,582,638 A * 6/1971 Peters
5,312,249 A    5/1994 Kennedy ..................... 433/29
5,498,260 A * 3/1996 Rink et al. ..................... 606/16

* cited by examiner

Primary Examiner—Cary E. O'Connor
(74) Attorney, Agent, or Firm—Dimock Stratton Clarizio; Mark B. Eisen

(57) ABSTRACT

A dental transilluminating device has a detachable plastic wand which serves as an optical waveguide and illumination aperture. The wand is configured to allow a wide variety of illumination apertures by cutting the tip of the wand at any desired position and/or angle, to allow for flexibility in both localization of the light beam and angle of approach against the lingual surface of the teeth, gums and other structures and tissues. A preferred embodiment of the invention uses an inexpensive self-contained battery-powered light source, with plastic optical wands that are easy to detach and sterilize, and are optionally disposable.

19 Claims, 1 Drawing Sheet

Fig. 1

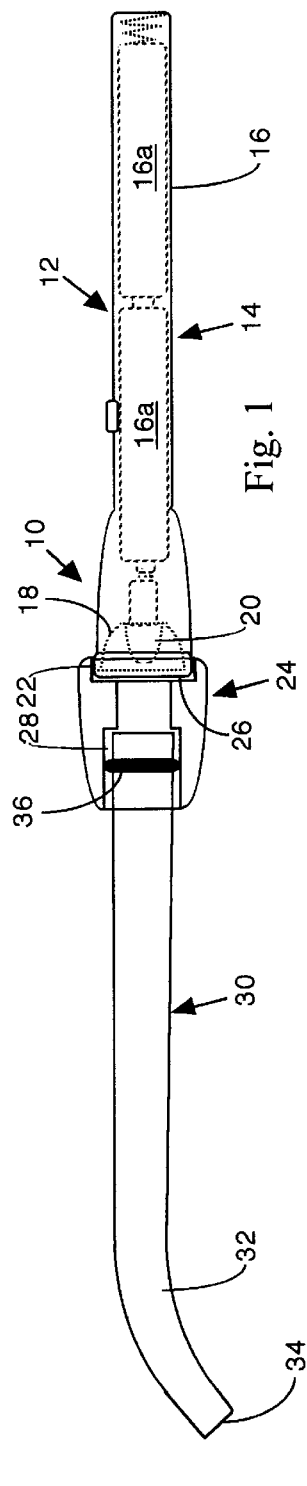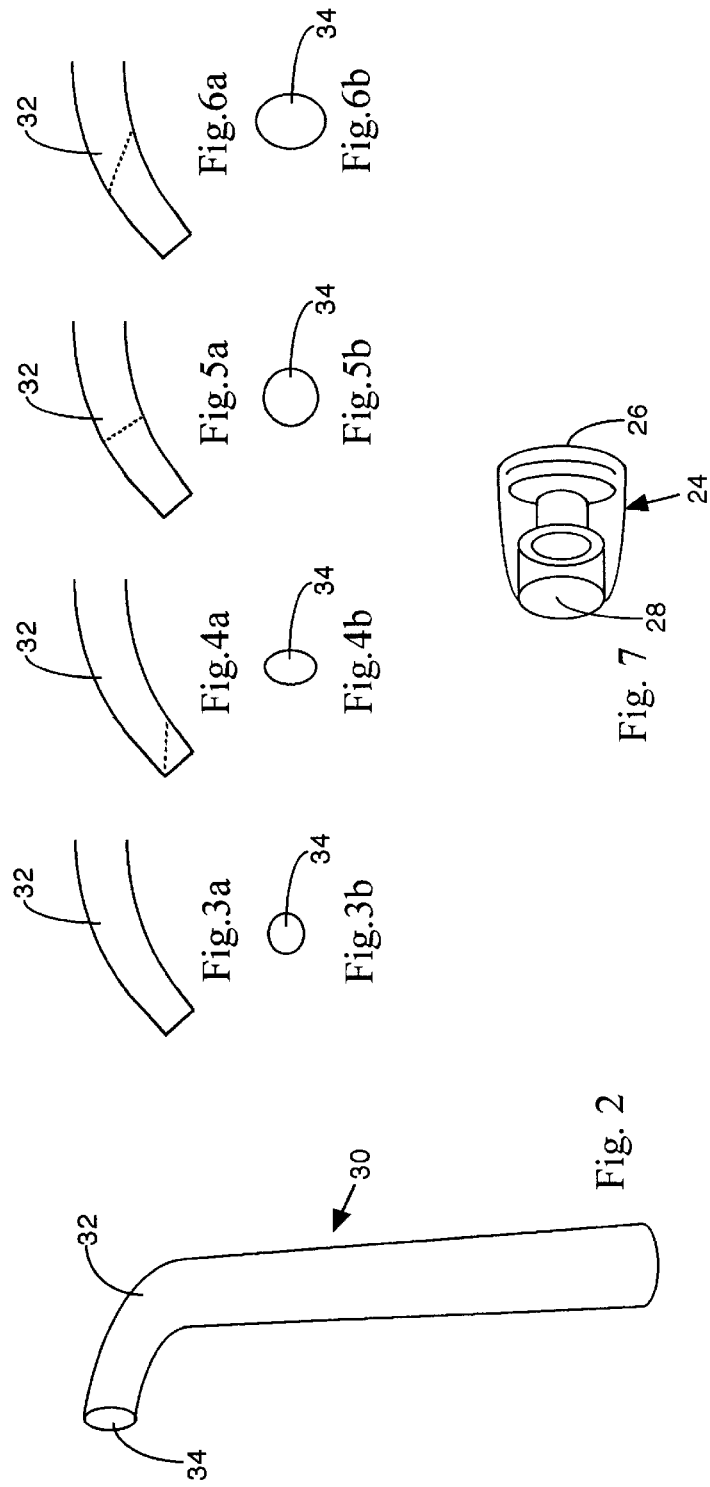

HAND-HELD DENTAL TRANSILLUMINATING DEVICE

FIELD OF INVENTION

This invention relates to dental equipment. In particular, this invention relates to a dental transilluminator for the transillumination of teeth, gums and other tissues.

BACKGROUND OF THE INVENTION

Transillumination is a very useful and effective diagnostic tool which has been used in dentistry for many years. Although capable only of highlighting anomalies which can be detected by visible light, dental transillumination can be more effective than an x-ray in the diagnosis of certain disorders such as interproximal caries, recurrent decay and longitudinal fractures, which can be extremely difficult to see in an x-ray.

A typical dental transilluminating device has a directional light wand wired to a power supply. The wand is composed of stainless steel and has a hollow tip forming an aperture which projects beyond the light source, to confine the light beam and minimize unwanted light dispersion into the mouth. The wand is reusable and is cleaned and sterilized in an autoclave between uses.

Existing dental transilluminating devices are complex and expensive, and difficult to maneuver in the mouth. Moreover, such devices do not provide any practical way to vary the illumination aperture, which makes it difficult to confine the light beam to a localized area, for example an individual tooth or interstitial tissue.

The present invention overcomes these disadvantages by providing a dental transilluminating device having a detachable plastic wand which serves as an optical waveguide and illumination aperture. The wand is configured to allow a wide variety of illumination apertures by cutting the tip of the wand at any desired position and/or angle.

The device of the invention thus allows considerable flexibility in both localization of the light beam and angle of approach against the lingual surface of the teeth, gums and other structures and tissues. A preferred embodiment of the invention uses an inexpensive self-contained battery-powered light source, with plastic optical wands that are easy to detach and sterilize, and are optionally disposable.

The present invention thus provides a dental transilluminating device, comprising a light source, and an optical waveguide comprising a plastic wand having a tip defining an illumination aperture, detachably affixed to the light source, wherein the tip of the wand can be cut to a selected aperture configuration and angle in order to vary the illumination aperture.

The present invention further provides a dental transilluminating device comprising, in combination, a light source, and an optical waveguide comprising a plastic wand having a tip defining an illumination aperture, detachably affixed to the light source, wherein the tip of the wand can be cut to a selected aperture configuration and angle in order to vary the illumination aperture.

The present invention further provides a dental transilluminator attachment for a hand-held flashlight, comprising an optical waveguide comprising a plastic wand having a tip defining an illumination aperture, and an adapter for detachably affixing the wand to a flashlight, wherein the tip of the wand can be cut to a selected aperture configuration and angle in order to vary the illumination aperture of the wand.

In further aspects of the invention, the optical waveguide is formed from a clear plastic; a portion of the wand has generally circular cross-section; the wand tapers toward the tip; the light source is self-contained and battery-powered; the light source is a flashlight; an adapter is provided for detachably affixing the wand to the light source; and/or the wand is disposable.

BRIEF DESCRIPTION OF THE DRAWINGS

In drawings which illustrate by way of example only a preferred embodiment of the invention, FIG. 1 is a side elevation of the device according to the invention, FIG. 2 is a perspective view of an optical wand according to the invention, FIG. 3a is an elevational view of an optical wand cut to produce the illumination aperture illustrated in FIG. 3b, FIG. 4a is an elevational view of an optical wand cut to produce the illumination aperture illustrated in FIG. 4b, FIG. 5a is an elevational view of an optical wand cut to produce the illumination aperture illustrated in FIG. 5b, FIG. 6a is an elevational view of an optical wand cut to produce the illumination aperture illustrated in FIG. 6b, and FIG. 7 is a perspective view of a preferred embodiment of an adapter for attaching the light wand to a light source.

DETAILED DESCRIPTION OF THE INVENTION

FIG. 1 illustrates a preferred embodiment of a dental transilluminating device 10 according to the invention. The device 10 comprises a light source 12 and an optical wand 30 detachably affixed to the light source 12.

The light source 12 in the preferred embodiment is self-contained and preferably small, comprising a casing 14 housing a battery compartment 16 and a reflector 18 within which is mounted a light bulb 20. A flashlight operating on two size "AA" batteries 16a, for example, has been found to be satisfactory, in which case the light source 12 may also have a cap 22 retaining the reflector 18 and may have a transparent cover (not shown).

The optical wand 30, shown in FIG. 2, is preferably formed (for example molded) from an inexpensive clear plastic, which is safe for use around tissue and withstands repeated cold sterilization. In the preferred embodiment the optical wand 30 has a bent or curved end portion 32 which directs light at an angle relative to the optical axis of the light source 12, to facilitate maneuverability within the mouth. The end portion 32 preferably has a generally circular cross-section which tapers toward the tip 34, as shown in FIG. 2. The optical wand 30 serves as a waveguide, confining light from the light source 12 by total internal reflection so that light escapes only from the tip 34, which thus defines the illumination aperture of the device 10.

The optical wand 30 is affixed to the light source 12, for example using a rigid or resilient adapter 24, shown in FIG. 7. The adapter 24 may be affixed to the light source 12 in any suitable fashion, for example by threaded engagement, slip fit, interference fit or otherwise. The adapter 24 may be formed from a compound which is resilient, for example a molded silicone compound, optionally having a relatively high coefficient of friction to provide strong frictional engagement to the light source 12 if a slip fit connection is used. Alternatively, the adapter 24 may be formed from metal, for example anodized aluminum, or another rigid material such as plastic, in which case threaded engagement to the light source 12 may provide a more stable connection.

The illustrated adapter 24 comprises a socket 26 into which the light source 12 is inserted in optical communication with a socket 28 into which the optical wand 30 is mounted, preferably (but not necessarily) in slip fit arrangement. The base of the optical wand 30 may be provided with a resilient retaining member such as an O-ring or washer 36 to detachably engage the wand 30 into the socket 26 of the adapter 24, preferably so that the wand 30 is rotatable about its base.

The optical wand may be supplied in a 'standard' length and configuration, for example as shown in FIG. 3a, having an illumination aperture as shown in FIG. 3b. The tip 34 of the optical wand 30 can then be cut in order to vary the size, angle and/or configuration of the illumination aperture. The size of the illumination aperture is in part determined by the axial position of the tip 34 along the optical wand 30, and both the size and configuration of the illumination aperture depend on the angle of the tip 34 relative to the longitudinal axis of the end portion 32 at the position of the tip 34. FIGS. 4a to and 4b, 5a and 5b and 6a and 6b respectively show by way of example three different aperture configurations and sizes created by cutting the tip 34 of the wand 30 in different axial positions and at different angles, as shown by the broken line in FIGS. 4a, 5a and 6a.

Since the optical wand 30 is inexpensive, a dentist can cut an optical wand 30 as needed during treatment of a patient. The wand 30 is optionally disposable, or the dentist may stock optical wands 30 with different illumination apertures which can be cold sterilized for reuse.

In use, the adapter 24 is affixed to the light source 12 by inserting the casing 14 into the socket 26. An optical wand 30 having an illumination aperture of the desired size, angle and configuration is mounted to the socket 28. The dentist turns on the light source 12, inserts the portion 32 into the patient's mouth and positions the tip 34 against the region to be transilluminated. During use the optical wand 30 may optionally be covered with a transparent flexible membrane such as plastic wrap (not shown), which is sterile and disposable.

Light from the light source 12 is guided through the optical wand 30 and escapes through the tip 34, illuminating the structures and/or tissues in front of the illumination aperture. If an optical wand 30 with a suitable illumination aperture is not in the dentist's inventory, the dentist can merely cut an optical wand 30, for example using a small saw, to create a tip 34 which provides an illumination aperture of the desired angle, size and configuration. The angle of the tip 34 may also be selected to allow for an easier approach, to facilitate use in the less accessible areas of the mouth, or may be selected solely for the desired size and/or configuration of the illumination aperture.

The device 10 can be sold as a kit including the light source 12, adapter 24 and one or more optical wands 30, optionally with separately packaged additional wands: 30 of the same or varying configurations. The optical wands 30 may also be sold separately for retrofitting to a commercially available flashlight or other light source 12, with a suitable adapter 24.

The invention can be used as a transilluminating device by itself, or can be employed in conjunction with an intraoral camera to improve visibility within the field of view.

A preferred embodiment of the invention having been thus described by way of example only, it will be apparent to those skilled in the art that certain modifications and adaptations may be made without departing from the scope of the invention, as set out in the claims.

I claim:

1. A dental transilluminating device, comprising a light source having an optical axis, and an optical waveguide comprising a plastic wand detachably affixed to the light source, having a tip defining an illumination aperture having a fixed angle relative to the optical axis of the light source, wherein the tip of the wand can be cut to a selected aperture configuration and angle in order to vary the illumination aperture.

2. The device of claim 1 in which the optical waveguide is formed from a clear plastic.

3. The device of claim 1 in which a portion of the wand has generally circular cross-section.

4. The device of claim 3 in which the wand tapers toward the tip.

5. The device of claim 1 in which the light source is self-contained and battery-powered.

6. The device of claim 5 in which the light source is a flashlight.

7. The device of claim 5 including an adapter for detachably affixing the wand to the light source.

8. The device of claim 1 in which the wand is disposable.

9. A dental transilluminating device comprising, in combination, a light source having an optical axis, and an optical waveguide comprising a plastic wand having a tip defining an illumination aperture having an angle fixed relative to the optical axis of the light source, detachably affixed to the light source by an adapter affixed to the light source along the optical axis of the light source, wherein the tip of the wand can be cut to a selected aperture configuration and angle in order to vary the illumination aperture.

10. The combination of claim 9 in which the optical waveguide is formed from a clear plastic.

11. The combination of claim 9 in which a portion of the wand has generally circular cross-section.

12. The combination of claim 11 in which the wand tapers toward the tip.

13. The combination of claim 9 in which the light source is self-contained and battery-powered.

14. The combination of claim 13 in which the light source is a flashlight.

15. The combination of claim 9 in which the wand is disposable.

16. A dental transilluminator attachment for a hand-held flashlight having an optical axis, comprising an optical waveguide comprising a plastic wand having a tip defining an illumination aperture having an angle fixed relative to the optical axis of the light source, and an adapter for detachably affixing the wand to the flashlight along the optical axis, wherein the tip of the wand can be cut to a selected aperture configuration and angle in order to vary the illumination aperture of the wand.

17. The combination of claim 16 in which the optical waveguide is formed from a clear plastic.

18. The combination of claim 16 in which a portion of the wand has generally circular cross-section.

19. The combination of claim 18 in which the wand tapers toward the tip.

* * * * *